(12) United States Patent

Richter

(10) Patent No.: US 10,131,736 B2
(45) Date of Patent: Nov. 20, 2018

(54) METHOD FOR ISOCYANATE MODIFICATION USING CATALYSTS WITH AN NPN SEQUENCE

(71) Applicant: Covestro Deutschland AG, Leverkusen (DE)

(72) Inventor: Frank Richter, Leverkusen (DE)

(73) Assignee: Covestro Deutschland AG, Leverkusen (DE)

( * ) Notice: Subject to any disclaimer, the term of this patent is extended or adjusted under 35 U.S.C. 154(b) by 64 days.

(21) Appl. No.: 15/119,179

(22) PCT Filed: Feb. 13, 2015

(86) PCT No.: PCT/EP2015/053085
§ 371 (c)(1),
(2) Date: Aug. 16, 2016

(87) PCT Pub. No.: WO2015/124503
PCT Pub. Date: Aug. 27, 2015

(65) Prior Publication Data
US 2017/0008996 A1 Jan. 12, 2017

(30) Foreign Application Priority Data
Feb. 18, 2014 (EP) .................................... 14155524

(51) Int. Cl.
| | |
|---|---|
| C08G 18/02 | (2006.01) |
| C08G 18/18 | (2006.01) |
| C07F 9/06 | (2006.01) |
| C08G 18/73 | (2006.01) |
| C08G 18/09 | (2006.01) |

(52) U.S. Cl.
CPC .......... *C08G 18/1883* (2013.01); *C07F 9/067* (2013.01); *C08G 18/02* (2013.01); *C08G 18/022* (2013.01); *C08G 18/027* (2013.01); *C08G 18/092* (2013.01); *C08G 18/095* (2013.01); *C08G 18/097* (2013.01); *C08G 18/73* (2013.01)

(58) Field of Classification Search
CPC .. C08G 18/1883; C08G 18/02; C08G 18/022; C08G 18/027; C08G 18/092; C08G 18/095; C08G 18/097
See application file for complete search history.

(56) References Cited

U.S. PATENT DOCUMENTS

| | | | |
|---|---|---|---|
| 4,960,848 A | 10/1990 | Scholl et al. | |
| 5,013,838 A | 5/1991 | Scholl | |
| 5,260,436 A | 11/1993 | Verkade et al. | |
| 5,914,383 A | 6/1999 | Richter et al. | |
| 6,090,939 A | 7/2000 | Richter et al. | |
| 6,107,484 A | 8/2000 | Richter et al. | |
| 2003/0135007 A1 | 7/2003 | Ewald et al. | |
| 2006/0241300 A1 | 10/2006 | Wessel et al. | |
| 2015/0025268 A1 | 1/2015 | Richter et al. | |

FOREIGN PATENT DOCUMENTS

| | | |
|---|---|---|
| CA | 2244486 A1 | 2/1999 |
| CN | 102964566 B | 3/2013 |
| CN | 102964566 B * | 5/2014 |

(Continued)

OTHER PUBLICATIONS

Document N_English Translation Dec. 13, 2017.*
The Synthesis of Aliphatic Polyisocyanates Containing Biuret, Isocyanurate or Uretdione Backbones for use in Coatings, Laas, et al., J. Prakt Chem., 1994, 336, 185-200.
1,4,2-Diazaphospholidine-3,5-diones and Related Compounds: A Lecture on Unpredictability in Catalysis, Frank U. Richter, Chem. Eur. J. 2009, 15, pp. 5200-5202.
D. Wendisch, H. Reiff and D. Dieterich, Die Angewandte Makromolekulare Chemie 141, 1986, 173-183 (Nr. 2302).
Anhydrous Phosphazenium Fluorides as Sources for Extremely Reactive Fluoride Ions in Solution, Schwesinger, et al., Chem. Eur. J. 2006, 12, 438-445.
An Electron-Rich Proazaphosphatrane for Isocyanate Trimerization to Isocyanurates, Raders, et al., J. Org. Chem. 2010, 75, 5308-5311.
Extremely Base-Resistant Organic Phosphazenium Cations, Schwesinger, et al, Chem Eur. J. 2006, 12, 429-437.

*Primary Examiner* — Michael L Leonard
(74) *Attorney, Agent, or Firm* — Richard P. Bender; John E. Mrozinski, Jr.

(57) ABSTRACT

The invention relates to a method for modifying isocyanates, wherein at least one organic monomer isocyanate having an NCO functionality >1 is oligomerised in the presence of at least one catalyst, said method being characterised in that the catalyst comprises at least one specific compound having an NPN sequence selected from compounds of formula I (formula I), and/or from compounds of formula II (formula II) where HX represents an acid with a pKa value ≥2, X⁻ represents the anion of an acid with a pKa value ≥2, and n represents an integer or fractional number between 0 and 20, wherein Y represents $R_{12}(R_{13})N$— and/or one or more substituents of the structure of formula III (formula III) and wherein $R_1$ to $R_{19}$ independently represent identical or different substituents selected from $C_1$-$C_{20}$ alkyl-, $C_1$-$C_{20}$ cycloalkyl- and $C_6$-$C_{20}$ aryl groups, or wherein $R_1$ and $R_2$, $R_3$ and $R_4$, $R_5$ and $R_6$, $R_7$ and $R_8$, $R_9$ and $R_{10}$, $R_{12}$ and $R_{13}$, $R_{14}$ and $R_{15}$, $R_{16}$ and $R_{17}$, $R_{18}$ and $R_{19}$ independently represent identical or different substituents selected from $C_1$-$C_{20}$ alkylene-, $C_1$-$C_{20}$ cycloalkylene-, $C_6$-$C_{20}$ arylene groups, and can form a 3- to 12-membered ring with the N atom joined to the P atom. The invention also relates to the use of a catalyst of this type.

15 Claims, No Drawings

(56) References Cited

FOREIGN PATENT DOCUMENTS

| EP | 0235388 | A2 | 9/1987 |
| EP | 0295926 | A2 | 12/1988 |
| EP | 0315692 | A1 | 5/1989 |
| EP | 0447074 | A2 | 9/1991 |

* cited by examiner

METHOD FOR ISOCYANATE MODIFICATION USING CATALYSTS WITH AN NPN SEQUENCE

CROSS-REFERENCE TO RELATED APPLICATIONS

This application is a national stage application (under 35 U.S.C. § 371) of PCT/EP2015/053085, filed Feb. 13, 2015, which claims benefit of European Application No. 14155524.3, filed Feb. 18, 2014, both of which are incorporated herein by reference in their entirety.

FIELD OF THE INVENTION

The invention relates to a process for modifying isocyanates, in which at least one monomeric organic isocyanate having an NCO functionality of >1 is oligomerized in the presence of at least one catalyst, and to the use of such a catalyst.

BACKGROUND OF THE INVENTION

The oligo- or polymerization of isocyanates, especially to form higher molecular weight oligomer mixtures having uretdione ("dimer"), isocyanurate ("trimer") and/or iminooxadiazinedione structures ("asymmetric trimer") in the molecular skeleton, collectively called isocyanate modification here, has long been known. If the modified polyisocyanates contain free NCO groups, which optionally may also have been temporarily deactivated with blocking agents, they are exceptionally high-quality starting materials for the production of a multitude of polyurethane plastics and coating compositions.

In a series of industrial methods for isocyanate modification which have become established, the isocyanate to be modified, usually a diisocyanate, is generally converted by addition of catalysts and these are then rendered inactive (deactivated) by suitable measures when the desired degree of conversion of the isocyanate to be modified has been attained, and the polyisocyanate obtained is generally separated from unreacted monomer. A summary of these methods from the prior art can be found in H. J. Laas et al., *J. Prakt. Chem.* 1994, 336, 185 ff.

Useful modification catalysts have been found to be neutral bases and compounds of ionic composition. The latter can usually be used in a very small amount and lead extremely rapidly to the desired result. In the case of the neutral bases, depending on the monomer to be converted and the neutral base used, this is not always true, but it is virtually impossible to infer structure-effect or -activity relationships (cf. *Chem. Eur. J.* 2009, 15, 5200-5202).

The option of also using tetraorganylammonium or -phosphonium as cation to the anion which is catalytically active toward isocyanates, such as hydroxide, alkanoate, alkoxylate, etc., is common knowledge, although generally not explicitly emphasized as being particularly preferred; cf. H. J. Laas et al., *J. Prakt. Chem.* 1994, 336, 185 ff.

Additionally known is the use of fluorides and hydrogenpolyfluorides, the latter being stable adducts of HF with compounds containing fluoride ions, optionally also in the form of their ammonium or phosphonium salts, for the isocyanate modification, from documents including EP 962 455 A1, EP 962 454 A1, EP 896 009 A1, EP 798 299 A1, EP 447 074 A1, EP 379 914 A1, EP 339 396 A1, EP 315 692 A1, EP 295 926 A1 and EP 235 388 A1.

However, the tetraorganylammonium and -phosphonium (hydrogenpoly)fluorides of the prior art, in the performance of the modification reaction, often have the disadvantage that, when they are used, the reaction can sometimes be maintained only with continuous metered addition of catalyst, meaning that the breakdown of the catalyst in the isocyanate medium proceeds unacceptably quickly for technical purposes compared to the modification reaction.

This disadvantage is not even always eliminated in a satisfactory manner by addition of aminosilanes to substances including fluoride ions, as described in EP 1 318 160 A1. It is possible that the compounds described as fluoride source therein are inactive without addition of aminosilanes or do not have sufficient activity for the isocyanate trimerization.

U.S. Pat. No. 5,260,436 B discloses the catalyzed reaction of aromatic isocyanates with specific bicyclic bases having P—N bonds (called phosphatranes) to give isocyanurates. However, J. Org. Chem. 2010, 75, 5308-5311 explicitly points out that the corresponding reaction with aliphatic isocyanates does not take place.

According to the teaching of CN 102964566, asymmetric trimer-containing products are obtainable, although the activity of the catalysts is generally unacceptably low for industrial implementation of the process, and catalyst breakdown occurs extremely rapidly with formation of carcinogenic phosphoramides, e.g. HMP. This is demonstrated in comparative example 5 of the present application. Furthermore, the process products of CN 102964566—in contrast with statements to the contrary in the cited document—are highly contaminated with troublesome by-products, especially with uretonimines.

EP 2 415 795 A1 describes very stable tetraorganylphosphonium (hydrogenpoly)fluorides that do not have these disadvantages, but they are not commercially available and are preparable only with difficulty.

DETAILED DESCRIPTION OF THE INVENTION

It was an object of the invention to provide an improved process for isocyanate modification, in which compounds that have good commercial availability or are easily preparable from inexpensive reactants are used as catalysts, these having a high catalytic activity and selectivity with simultaneously good catalyst stability.

This object is achieved by a process for modifying isocyanates, in which at least one monomeric organic isocyanate having an NCO functionality of >1 is oligomerized in the presence of at least one catalyst, wherein the process is characterized in that the catalyst comprises at least one compound having an N—P—N sequence, selected from compounds of the formula I

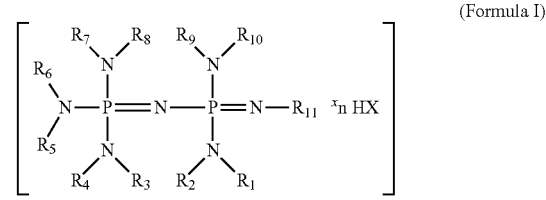

(Formula I)

and/or compounds of the formula II

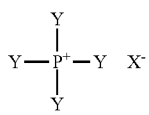
(Formula II)

in which HX is an acid having a pKa≥2, X⁻ is the anion of an acid having a pKa≥2 and n is an integer or fraction from 0 to 20,
in which Y is $R_{12}(R_{13})N$— and/or one or more substituents of the structure of the formula III

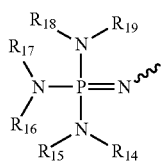
(Formula III)

and
where $R_1$ to $R_{19}$ are independently identical or different substituents selected from $C_1$-$C_{20}$-alkyl, $C_1$-$C_{20}$-cycloalkyl and $C_6$-$C_{20}$-aryl groups or
where $R_1$ and $R_2$, $R_3$ and $R_4$, $R_5$ and $R_6$, $R_7$ and $R_8$, $R_9$ and $R_{10}$, $R_{12}$ and $R_{13}$, $R_{14}$ and $R_{15}$, $R_{16}$ and $R_{17}$, $R_{18}$ and $R_{19}$ are independently identical or different substituents selected from $C_1$-$C_{20}$-alkylene, $C_1$-$C_{20}$-cycloalkylene, $C_6$-$C_{20}$-arylene groups and may, together with the P-bonded N atom, form a 3- to 12-membered ring.

By the modification process of the invention, a wide range of high-quality polyisocyanates, which are therefore very valuable for the polyurethane sector, is very generally obtainable in a simple manner. Depending on the starting (di)isocyanate used and the reaction conditions, the process of the invention affords polyisocyanates of the isocyanate trimer type (i.e. containing isocyanurate and/or iminooxadiazinedione structures) having a low proportion of uretdione groups ("isocyanate dimers"). With rising reaction temperature, the proportion of the latter in the process products generally rises.

In the context of the present invention, N—P—N sequence means that the compound has a nitrogen-phosphorus-nitrogen atom sequence, where single or else multiple bonds may be present between these atoms. It is also possible for one or else more than one atom in this sequence to bear a positive or negative charge.

In the process of the invention, the 3-12-membered ring may contain at least one heteroatom selected from N, O and S and/or a substituent having such a heteroatom.

X⁻ may, for example, be OH⁻, F⁻ or the anion of alcohols, phenols and alkanoic acids. Analogously, HX may be $H_2O$, HF or an alcohol, a phenol or an alkanoic acid. The acid HX or the acid corresponding to the anion X⁻ may especially have a pKa≥2.5, preferably ≥3.0 or even ≥3.10.

In an advantageous configuration of the process of the invention, n is an integer or fraction from 1 to 10.

In the process of the invention, it may further be the case that the oligomerization is conducted in the presence of a solvent and/or additive.

For performance of the process of the invention, it is possible in principle to use any known monomeric mono-, di- or polyisocyanates from the prior art, individually or in any desired mixtures with one another. Examples include: hexamethylene diisocyanate (HDI), 2-methylpentane 1,5-diisocyanate, 2,4,4-trimethylhexane 1,6-diisocyanate, 2,2,4-trimethylhexane 1,6-diisocyanate, 4-isocyanatomethyloctane 1,8-diisocyanate, 3(4)-isocyanatomethyl-1-methylcyclohexyl isocyanate (IMCI), isophorone diisocyanate (IPDI), 1,3- and 1,4-bis(isocyanatomethyl)benzene (XDI), 1,3- and 1,4-bis(isocyanatomethyl)-cyclohexane (H6XDI), tolylene 2,4- and 2,6-diisocyanate (TDI), bis(4-isocyanatophenyl)methane (4,4'MDI), 4-isocyanatophenyl-2-isocyanato-phenylmethane (2,4'MDI) and polycyclic products obtainable by formaldehyde-aniline polycondensation and subsequent conversion of the resulting (poly) amines to the corresponding (poly)isocyanates (polymer MDI).

Preference is given to monomeric aliphatic diisocyanates, i.e. diisocyanates in which both NCO groups are bonded to an $sp^3$-hybridized carbon atom. Particular preference is given to hexamethylene diisocyanate (HDI), 2-methylpentane diisocyanate, 2,4,4-trimethylhexane 1,6-diisocyanate, 2,2,4-trimethylhexane 1,6-diisocyanate, 4-isocyanatomethyloctane 1,8-diisocyanate, 3(4)-isocyanatomethyl-1-methylcyclohexyl isocyanate (IMCI), isophorone diisocyanate (IPDI), 1,3- and 1,4-bis(isocyanatomethyl)benzene (XDI) and 1,3- and 1,4-bis(isocyanatomethyl)-cyclohexane (H6XDI).

For the present invention, it is possible to use all the aforementioned isocyanates, irrespective of the method by which they have been prepared, i.e. whether they have been produced, for example, with or without use of phosgene.

The amount of the catalyst to be used in the process of the invention is guided primarily by the isocyanate used and the desired reaction rate and is preferably 0.001 to 5 mol %, based on the sum total of the molar amounts of the monomeric isocyanate used and the catalyst. Preference is further given to using 0.002 to 2 mol % of catalyst.

In the method according to the invention, the catalyst may be used undiluted or dissolved in solvents. Useful solvents are all compounds which do not react with the catalyst and are capable of dissolving it to a sufficient degree, for example aliphatic or aromatic hydrocarbons, alcohols, esters and ethers. Preference is given to using alcohols.

The process of the invention can be effected within the temperature range from 0° C. to +250° C., preferably 20 to 180° C., more preferably 40 to 150° C., and can be interrupted at any degree of conversion, preferably after 5% to 80%, more preferably 10% to 60%, of the monomeric isocyanate used has been converted.

Catalyst deactivation can be accomplished in principle by employing a whole series of previously described prior art methods, for example the addition of (sub- or super-) stoichiometric amounts of strong acids or acid derivatives (e.g. benzoyl chloride, acidic esters of phosphorus- or sulfur-containing acids, these acids themselves, but not HF), absorptive binding of the catalyst and subsequent removal by filtration, and other methods known to those skilled in the art.

Compared to catalysis by catalysts based on simple quaternary phosphonium salts, for example those with a tetra-n-butylphosphonium cation (see comparative examples 1a to 1d), a distinct improvement in catalyst service life is observed in the process of the invention and otherwise identical reaction conditions, and this does not decline as significantly with rising temperature as in the case of the abovementioned prior art compounds. This is illustrated in the examples and comparative examples by the turnover frequency (TOF). The latter is based on the molar amount of NCO groups A converted in the oligomerization, the molar amount of catalyst B needed for the purpose and the reaction time t (measured in seconds) according to the following equation:

$$TOF = A*(B*t)^{-1} [mol*(mol*sec)^{-1}].$$

In a particular continuously operated embodiment of the process of the invention, the oligomerization can be undertaken in a tubular reactor.

It is particularly surprising that neutral bases having at least one N—P—N—P—N unit, for example $(Me_2N)_3$P=N—P(NMe$_2$)$_2$=NEt or $(Me_2N)_3$P=N—P(NMe$_2$)$_2$=N$^t$Bu, do not exhibit any tendencies to break down in the isocyanate medium, like their equivalents having one =(R$_2$N)$_2$P unit fewer (cf. CN 102964566 and comparative example 5), and even the FIX adducts onto these neutral bases (for the definition of X see further up in the text), which are extremely simple to prepare, are catalytically active. This is not true of adducts of weak acids such as HF, acetic acid and pivalic acid onto neutral catalyst bases such as tributylphosphine, pyridine, tributylamine and the P1 bases of CN 102964566, these having known—albeit sometimes very slight—activity for the isocyanate modification (comparative example 6). In a particularly preferred configuration of the process of the invention, therefore, the compound having N—P—N—P—N sequence is selected from compounds of the formula $(Me_2N)_3$P=N—P(NMe$_2$)$_2$=NR$_{20}$ where R$_{20}$ is as defined for R$_{11}$, especially $(Me_2N)_3$P=N—P(NMe$_2$)$_2$=NEt, $(Me_2N)_3$P=N—P(NMe$_2$)$_2$=N$^t$Bu, or mixtures thereof and of their HX adducts, where HX is especially selected from HF.

In a further configuration of the process of the invention, the cation of the compound having an N—P—N sequence of formula II corresponds to the following formula IV:

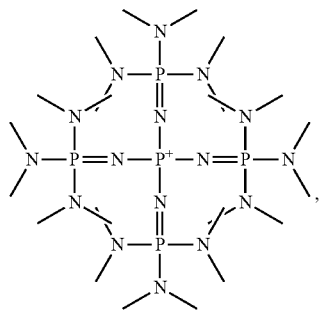

(Formula IV)

where X$^-$ is especially selected from F$^-$, HF$_2^-$, H$_2$F$_3^-$ and mixtures of these. In formula IV, the terminal amino groups are thus dimethylamino groups of the following formula V:

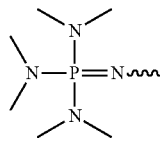

(Formula V)

The IUPAC name of the cation of the formula IV is 1,1,1,5,5,5-hexakis(dimethylamino)-3,3-bis{[tris(dimethylamino)-lambda$^5$-phosphanylidene]amino}-1lambda$^5$,5lambda$^5$-triphosphaza-1,4-dien-3-ium.

Most preferably, the catalyst comprises or consists of the following compound of the formula VI, i.e. consists of a compound having the cation of the formula IV and fluoride as anion and the HF adducts thereof (difluorides, trifluorides, etc.):

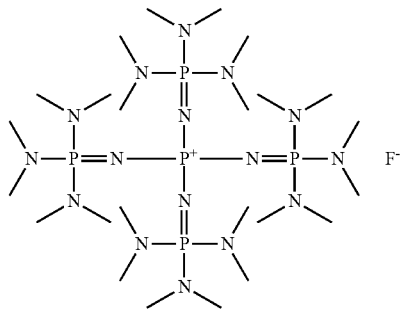

(Formula VI)

A quite general observation with rising HF content in the adducts of the invention is a rising selectivity with respect to the formation of asymmetric trimers (iminooxadiazinediones), whereas O-containing anions lead to virtual exclusive formation of isocyanurates.

The products or product mixtures obtained by the process of the invention are consequently versatile starting materials for production of optionally foamed plastic(s) and of paints, coating compositions, adhesives and additives. They are especially suitable for production of optionally water-dispersible one- and two-pack polyurethane paints, optionally in NCO-blocked form, because of their reduced solution and melt viscosity in comparison to (predominantly) isocyanurate polyisocyanate-based products with an otherwise equivalent or improved profile of properties. Thus, the HDI-based process products of the invention, even in high dilution in paint solvents, are more stable to the occurrence of flocculation or turbidity than corresponding prior art products.

The process products of the invention can be used pure or in conjunction with other prior art isocyanate derivatives, such as polyisocyanates containing uretdione, biuret, allophanate, isocyanurate and/or urethane groups, wherein the free NCO groups have optionally been deactivated with blocking agents.

The present invention is further directed to the use of a catalyst comprising a compound having an N—P—N sequence, selected from compounds of the formula I

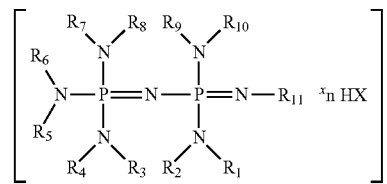

(Formula I)

and/or compounds of the formula II

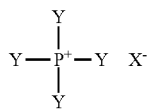

(Formula II)

in which HX is an acid having a pKa≥2, X$^-$ is the anion of an acid having a pKa≥2 and n is an integer or fraction from 0 to 20, in which Y is $R_{12}(R_{13})N$— and/or one or more substituents of the structure of the formula III

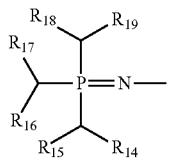
(Formula III)

and where $R_1$ to $R_{19}$ are independently identical or different substituents selected from $C_1$-$C_{20}$-alkyl, $C_1$-$C_{20}$-cycloalkyl and $C_6$-$C_{20}$-aryl groups or where $R_1$ and $R_2$, $R_3$ and $R_4$, $R_5$ and $R_6$, $R_7$ and $R_8$, $R_9$ and $R_{10}$, $R_{12}$ and $R_{13}$, $R_{14}$ and $R_{15}$, $R_{16}$ and $R_{17}$, $R_{18}$ and $R_{19}$ are independently identical or different substituents selected from $C_1$-$C_{20}$-alkylene, $C_1$-$C_{20}$-cycloalkylene, $C_6$-$C_{20}$-arylene groups and may, together with the P-bonded N atom, form a 3- to 12-membered ring, for oligomerization of monomeric organic isocyanates having an NCO functionality >1.

The present invention is elucidated in detail hereinafter by examples and comparative examples, but without restricting it thereto.

EXAMPLES

All percentages, unless noted otherwise, are understood to mean percent by weight.

Conclusions relating to structural product composition were determined by NMR spectroscopy. The measurements were effected on the Bruker DPX 400 or DRX 700 instruments on 5% ($^1$H NMR) or about 50% ($^{13}$C NMR) samples in dry $C_6D_6$ at a frequency of 400 or 700 MHz ($^1$H NMR) or 100 or 176 MHz ($^{13}$C NMR). The reference employed for the ppm scale was small amounts of tetramethylsilane in the solvent with $^1$H NMR chemical shift 0 ppm. Alternatively, the $C_6D_5H$ present in the solvent was used as reference signal: $^1$H NMR chemical shift 7.15 ppm; $^{13}$C NMR chemical shift 128.02 ppm. Data for the chemical shift of the compounds in question were taken from the literature (cf. D. Wendisch, H. Reiff and D. Dieterich, Die Angewandte Makromolekulare Chemie 141, 1986, 173-183 and literature cited therein and EP-A 896 009.

The residual monomer contents were determined by gas chromatography on the Agilent Technologies 6890 N Network GC system.

The phosphorus content of all samples was determined by x-ray fluorescence analysis (XFA) on the Bruker AXS S8 Tiger instrument without prior digestion (direct measurement).

All reactions were conducted under a nitrogen atmosphere unless stated otherwise.

The diisocyanates used are products of Bayer MaterialScience AG, D-51368 Leverkusen; all other commercially available chemicals were sourced from Aldrich, D-82018 Taufkirchen.

The catalysts that are not commercially available were obtained by literature methods (Chem. Eur. J. 2006, 12, 429-437 and literature cited therein).

The turnover frequency (TOF) is defined by the following equation:

$$TOF = A*(B*t)^{-1} [\text{mol}*(\text{mol}*\text{sec})^{-1}].$$

The molar amount of the NCO groups A converted in the oligomerization is determined therein by titration in accordance with DIN 53 185.

B describes the molar amount of catalyst B used in the oligomerization, which is calculated from the starting weight.

T denotes the reaction rate in seconds.

Examples 1a to 1d

Comparative Examples

1a) Catalyst: tetra-n-butylphosphonium hydroxide, 0.8% in isopropanol
1b) Catalyst: tetra-n-butylphosphonium (hydrogen)difluoride, 70% in isopropanol
1c) Catalyst: tetra-n-butylphosphonium acetate, 22% in 2-ethylhexanol
1d) Catalyst: tetra-n-butylphosphonium pivalate, 23% in 2-ethylhexanol A jacketed flange vessel heated to the starting temperature desired in each case by means of an external circuit, having a stirrer, reflux condenser connected to an inert gas system (nitrogen/vacuum) and thermometer, was initially charged with 1000 g of HDI which was freed of dissolved gases by stirring under reduced pressure (<1 mbar) for one hour. After venting with nitrogen, the amount of catalyst specified in Table 1 was metered in such a way that the maximum temperature specified in Table 1 was not exceeded. After about 1 mol of NCO groups had been converted, as indicated by attainment of a refractive index (measured at 20° C.; $n_D^{20}$) between 1.4600 and 1.4620, the catalyst was deactivated by addition of an amount of p-toluenesulfonic acid (as a 50% solution in isopropanol) equivalent to the catalyst, and the mixture was stirred at reaction temperature for a further 30 min and subsequently worked up. The time between the first addition of catalyst and addition of the toluenesulfonic acid solution was used to calculate the TOF reported in Table 1 (as defined on Page 13, Lines 3-9). If multiple experiments were conducted at the same reaction temperature, the catalyst was metered in more slowly and in some cases also discontinuously in the first experiment in each case, in order to ascertain the optimal amount for the subsequent experiment. In the latter, the catalyst was metered in more rapidly, or the target conversion was attained even after addition of less catalyst and/or after a shorter time, which leads to higher TOF values.

The workup was effected by vacuum distillation in a thin film evaporator of the short-path evaporator (SPE) type with an upstream preliminary evaporator (PE) (distillation data: pressure: 0.08+/−0.04 mbar, PE temperature: 120° C., ME temp.: 140° C.), with separation of unconverted monomer as distillate and the low-monomer polyisocyanate resin as bottom product (starting run). The polyisocyanate resin was separated and the distillate was collected in a second flange stirring apparatus of identical construction to the first, and made up to the starting amount (1000 g) with freshly degassed HDI. Thereafter, the mixture was treated again with catalyst and the procedure as described at the outset was followed. This procedure was repeated several times with variation of the reaction temperature. The results can be found in Table 1.

TABLE 1

| Example no. | Catalyst cation | Catalyst anion | amount [g] | $n_D^{20}$ on addition of stopper | Reaction temperature [° C.] start | Reaction temperature [° C.] max. | TOF |
|---|---|---|---|---|---|---|---|
| 1a- A | n-Bu$_4$P | OH$^-$ | 13.1 | 1.4603 | 60 | 63 | 0.21 |
| 1a- B | n-Bu$_4$P | OH$^-$ | 10.8 | 1.4605 | 60 | 62 | 0.76 |
| 1a- C | n-Bu$_4$P | OH$^-$ | 27.6 | 1.4617 | 80 | 83 | 0.31 |
| 1a- D | n-Bu$_4$P | OH$^-$ | 26.5 | 1.4609 | 80 | 84 | 0.70 |
| 1a- E | n-Bu$_4$P | OH$^-$ | 61.9 | 1.4611 | 100 | 103 | 0.12 |
| 1a- F | n-Bu$_4$P | OH$^-$ | 46.7 | 1.4610 | 100 | 102 | 0.25 |
| 1b- A | n-Bu$_4$P | [HF$_2$]$^-$ | 0.4 | 1.4601 | 60 | 62 | 1.3 |
| 1b- B | n-Bu$_4$P | [HF$_2$]$^-$ | 0.3 | 1.4600 | 60 | 63 | 1.3 |
| 1b- C | n-Bu$_4$P | [HF$_2$]$^-$ | 0.5 | 1.4600 | 80 | 84 | 0.5 |
| 1b- D | n-Bu$_4$P | [HF$_2$]$^-$ | 1.1 | 1.4600 | 100 | 105 | 0.2 |
| 1b- E | n-Bu$_4$P | [HF$_2$]$^-$ | 3.9 | 1.4602 | 120 | 127 | 0.1 |
| 1b- F | n-Bu$_4$P | [HF$_2$]$^-$ | 11.9 | 1.4602 | 140 | 152 | 0.1 |
| 1c- A | n-Bu$_4$P | CH$_3$COO$^-$ | 6.0 | 1.4610 | 60 | 62 | 0.05 |
| 1c- B | n-Bu$_4$P | CH$_3$COO$^-$ | 4.7 | 1.4606 | 60 | 62 | 0.05 |
| 1c- C | n-Bu$_4$P | CH$_3$COO$^-$ | 8.1 | 1.4605 | 80 | 82 | 0.04 |
| 1c- D | n-Bu$_4$P | CH$_3$COO$^-$ | 9.0 | 1.4608 | 80 | 82 | 0.04 |
| 1c- E | n-Bu$_4$P | CH$_3$COO$^-$ | 15.3 | 1.4609 | 100 | 102 | 0.02 |
| 1c- F | n-Bu$_4$P | CH$_3$COO$^-$ | 15.3 | 1.4612 | 100 | 101 | 0.02 |
| 1d- A | n-Bu$_4$P | (CH$_3$)$_3$CCOO$^-$ | 5.1 | 1.4600 | 60 | 63 | 0.05 |
| 1d- B | n-Bu$_4$P | (CH$_3$)$_3$CCOO$^-$ | 6.8 | 1.4609 | 60 | 61 | 0.04 |
| 1d- C | n-Bu$_4$P | (CH$_3$)$_3$CCOO$^-$ | 20.9 | 1.4608 | 80 | 81 | 0.01 |
| 1d- D | n-Bu$_4$P | (CH$_3$)$_3$CCOO$^-$ | 13.4 | 1.4609 | 80 | 81 | 0.03 |
| 1d- E | n-Bu$_4$P | (CH$_3$)$_3$CCOO$^-$ | 16.6 | 1.4607 | 100 | 100 | 0.02 |
| 1d- F | n-Bu$_4$P | (CH$_3$)$_3$CCOO$^-$ | 16.4 | 1.4604 | 100 | 101 | 0.02 |

Finally, the phosphorus content of the distillate that remained at the end of a series conducted with identical catalyst was determined and the results provided in Table 2:

TABLE 2

| Example no. | Catalyst cation | Catalyst anion | P content of the distillate [ppm] |
|---|---|---|---|
| 1a- F | n-Bu$_4$P | OH– | 73 |
| 1b- F | n-Bu$_4$P | [HF$_2$]$^-$ | 730 |
| 1c- F | n-Bu$_4$P | CH$_3$COO$^-$ | 970 |
| 1d- F | n-Bu$_4$P | (CH$_3$)$_3$CCOO$^-$ | 1200 |

Examples 2a to 2e

Inventive

The procedure was as in Example 1, except that the catalysts used were salts with tris(dimethylamino)-N-[tris(dimethylamino)-lambda$^5$-phosphanylidene]-lambda$^5$-phosphaniminium cation, Me$_{12}$P$_2$N$_7^+$), each as about 10% solutions in isopropanol (3a: fluoride, 3b: difluoride, 3c: trifluoride, 3d: acetate, 3e: pivalate). The results can be found in Table 3. In none of the distillates was the phosphorus content above the detection limit (about 1 ppm).

TABLE 3

| Example no. | Catalyst anion | amount [g] | Reaction temperature [° C.] start | Reaction temperature [° C.] max. | TOF |
|---|---|---|---|---|---|
| 2a- A | F$^-$ | 1.5 | 60 | 65 | 8.9 |
| 2a- B | F$^-$ | 1.4 | 60 | 68 | 10.5 |
| 2a- C | F$^-$ | 1.0 | 80 | 86 | 7.5 |
| 2a- D | F$^-$ | 0.9 | 80 | 85 | 8.2 |
| 2a- E | F$^-$ | 0.8 | 100 | 110 | 5.6 |
| 2a- F | F$^-$ | 0.7 | 100 | 109 | 7.5 |
| 2b- A | [HF$_2$]$^-$ | 2.4 | 60 | 65 | 2.0 |
| 2b- B | [HF$_2$]$^-$ | 2.2 | 60 | 65 | 2.4 |
| 2b- C | [HF$_2$]$^-$ | 2.2 | 80 | 89 | 3.1 |
| 2b- D | [HF$_2$]$^-$ | 2.1 | 80 | 85 | 3.5 |
| 2b- E | [HF$_2$]$^-$ | 2.0 | 100 | 109 | 3.5 |
| 2b- F | [HF$_2$]$^-$ | 1.9 | 100 | 105 | 4.2 |
| 2c- A | [H$_2$F$_3$]$^-$ | 3.5 | 60 | 63 | 2.0 |
| 2c- B | [H$_2$F$_3$]$^-$ | 3.2 | 60 | 63 | 2.5 |
| 2c- C | [H$_2$F$_3$]$^-$ | 2.9 | 80 | 82 | 2.0 |
| 2c- D | [H$_2$F$_3$]$^-$ | 2.8 | 80 | 82 | 2.1 |
| 2c- E | [H$_2$F$_3$]$^-$ | 2.7 | 100 | 105 | 2.5 |
| 2c- F | [H$_2$F$_3$]$^-$ | 2.6 | 100 | 105 | 2.8 |
| 2d- A | CH$_3$COO$^-$ | 2.5 | 60 | 62 | 2.2 |
| 2d- B | CH$_3$COO$^-$ | 2.2 | 60 | 61 | 2.4 |
| 2d- C | CH$_3$COO$^-$ | 2.2 | 80 | 83 | 2.9 |
| 2d- D | CH$_3$COO$^-$ | 2.1 | 80 | 83 | 3.5 |
| 2d- E | CH$_3$COO$^-$ | 1.9 | 100 | 106 | 3.9 |
| 2d- F | CH$_3$COO$^-$ | 1.8 | 100 | 106 | 4.0 |
| 2e- A | (CH$_3$)$_3$CCOO$^-$ | 3.6 | 60 | 66 | 3.4 |
| 2e- B | (CH$_3$)$_3$CCOO$^-$ | 3.5 | 60 | 66 | 4.2 |
| 2e- C | (CH$_3$)$_3$CCOO$^-$ | 3.1 | 80 | 82 | 5.2 |
| 2e- D | (CH$_3$)$_3$CCOO$^-$ | 2.9 | 80 | 81 | 5.6 |
| 2e- E | (CH$_3$)$_3$CCO$^-$ | 2.8 | 100 | 101 | 5.9 |
| 2e- F | (CH$_3$)$_3$CCOO$^-$ | 2.8 | 100 | 101 | 6.5 |

Examples 3a to 3g

Inventive

The procedure was as in Example 1, except that the catalysts used were a) N''''—[P,P-bis(dimethylamino)-N-ethylphosphorimidoyl]-N,N,N,N,N'',N''-hexamethylphosphorimidic triamide as an about 10% solution in diethylene glycol di-n-butyl ether and the following more specific acid adducts thereof: b) fluoride (HF adduct onto neutral base), c): difluoride (adduct of 2 equivalents of HF onto neutral base), d): trifluoride (adduct of 3 equivalents of HF onto neutral base), e): acetate (acetic acid adduct onto neutral base), f): pivalate (pivalic acid adduct onto neutral base) g): hydroxide (water adduct onto neutral base). The results can be found in Table 4. In none of the distillates was the phosphorus content above the detection limit (about 1 ppm).

TABLE 4

| Example no. | Catalyst anion | amount [g] | Reaction temperature [° C.] start | max. | TOF |
|---|---|---|---|---|---|
| 3a- A | none (neutral base) | 5.0 | 60 | 69 | 0.7 |
| 3a- B | none (neutral base) | 4.2 | 60 | 62 | 1.4 |
| 3a- C | none (neutral base) | 4.1 | 80 | 85 | 1.8 |
| 3a- D | none (neutral base) | 3.9 | 80 | 83 | 2.0 |
| 3a- E | none (neutral base) | 3.7 | 100 | 105 | 2.5 |
| 3a- F | none (neutral base) | 3.5 | 100 | 103 | 2.9 |
| 3b- A | $F^-$ | 5.3 | 60 | 76 | 1.2 |
| 3b- B | $F^-$ | 5.0 | 60 | 62 | 2.5 |
| 3b- C | $F^-$ | 4.8 | 80 | 86 | 3.1 |
| 3b- D | $F^-$ | 4.5 | 80 | 82 | 3.5 |
| 3b- E | $F^-$ | 3.9 | 100 | 102 | 3.7 |
| 3b- F | $F^-$ | 3.5 | 100 | 100 | 3.9 |
| 3c- A | $[HF_2]^-$ | 3.5 | 60 | 78 | 6.2 |
| 3c- B | $[HF_2]^-$ | 2.8 | 60 | 75 | 7.5 |
| 3c- C | $[HF_2]^-$ | 2.5 | 80 | 88 | 8.3 |
| 3c- D | $[HF_2]^-$ | 2.2 | 80 | 82 | 8.5 |
| 3c- E | $[HF_2]^-$ | 2.2 | 100 | 105 | 9.5 |
| 3c- F | $[HF_2]^-$ | 1.8 | 100 | 102 | 8.5 |
| 3d- A | $[H_2F_3]^-$ | 2.7 | 60 | 62 | 0.8 |
| 3d- B | $[H_2F_3]^-$ | 3.2 | 60 | 63 | 1.2 |
| 3d- C | $[H_2F_3]^-$ | 3.2 | 80 | 85 | 1.5 |
| 3d- D | $[H_2F_3]^-$ | 3.0 | 80 | 84 | 1.8 |
| 3d- E | $[H_2F_3]^-$ | 2.8 | 100 | 105 | 2.5 |
| 3d- F | $[H_2F_3]^-$ | 2.8 | 100 | 104 | 3.2 |
| 3e- A | $CH_3COO^-$ | 3.8 | 60 | 65 | 1.0 |
| 3e- B | $CH_3COO^-$ | 3.2 | 60 | 63 | 1.8 |
| 3e- C | $CH_3COO^-$ | 3.2 | 80 | 88 | 1.9 |
| 3e- D | $CH_3COO^-$ | 2.9 | 80 | 85 | 2.2 |
| 3e- E | $CH_3COO^-$ | 2.8 | 100 | 105 | 2.8 |
| 3e- F | $CH_3COO^-$ | 2.5 | 100 | 105 | 3.3 |
| 3f- A | $(CH_3)_3CCOO^-$ | 4.0 | 60 | 65 | 1.1 |
| 3f- B | $(CH_3)_3CCOO^-$ | 3.5 | 60 | 63 | 1.7 |
| 3f- C | $(CH_3)_3CCOO^-$ | 3.2 | 80 | 85 | 1.8 |
| 3f- D | $(CH_3)_3CCOO^-$ | 2.5 | 80 | 86 | 2.0 |
| 3f- E | $(CH_3)_3CCOO^-$ | 2.5 | 100 | 110 | 2.2 |
| 3f- F | $(CH_3)_3CCOO^-$ | 2.4 | 100 | 105 | 2.8 |
| 3g- A | $OH^-$ | 2.8 | 60 | 68 | 1.8 |
| 3g- B | $OH^-$ | 2.5 | 60 | 65 | 2.5 |
| 3g- C | $OH^-$ | 2.2 | 80 | 85 | 3.5 |
| 3g- D | $OH^-$ | 2.0 | 80 | 88 | 3.8 |
| 3g- E | $OH^-$ | 1.8 | 100 | 108 | 4.2 |
| 3g- F | $OH^-$ | 1.6 | 100 | 110 | 4.5 |

Examples 4a to 4c

Inventive

The procedure was as in Example 1, except that the catalysts used in each case were about 10% solutions of 1,1,1,5,5,5-hexakis(dimethylamino)-3,3-bis{[tris(dimethylamino)-lambda$^5$-phosphanylidene]amino}-1lambda$^5$, 5lambda$^5$-triphosphaza-1,4-dien-3-ium fluoride in benzene (a) or the HF adduct thereof (b, difluoride) and the adduct thereof with 2 equivalents of HF (c, trifluoride). The results can be found in Table 5. In none of the distillates was the phosphorus content above the detection limit (about 1 ppm).

TABLE 5

| Example no. | Catalyst anion | amount [g] | Reaction temperature [° C.] start | max. | TOF |
|---|---|---|---|---|---|
| 4a- A | $F^-$ | 5.8 | 60 | 60 | 0.6 |
| 4a- B | $F^-$ | 5.4 | 60 | 60 | 0.8 |
| 4a- C | $F^-$ | 5.2 | 80 | 81 | 1.2 |
| 4a- D | $F^-$ | 5.0 | 80 | 81 | 1.4 |
| 4a- E | $F^-$ | 4.5 | 100 | 100 | 1.8 |
| 4a- F | $F^-$ | 4.2 | 100 | 100 | 2.2 |
| 4b- A | $[HF_2]^-$ | 12.8 | 60 | 63 | 0.9 |
| 4b- B | $[HF_2]^-$ | 11.5 | 60 | 62 | 1.1 |
| 4b- C | $[HF_2]^-$ | 11.0 | 80 | 83 | 1.4 |
| 4b- D | $[HF_2]^-$ | 10.5 | 80 | 82 | 1.6 |
| 4b- E | $[HF_2]^-$ | 10.4 | 100 | 103 | 1.8 |
| 4b- F | $[HF_2]^-$ | 9.8 | 100 | 104 | 2.2 |
| 4c- A | $[H_2F_3]^-$ | 7.0 | 60 | 69 | 3.4 |
| 4c- B | $[H_2F_3]^-$ | 6.5 | 60 | 65 | 4.2 |
| 4c- C | $[H_2F_3]^-$ | 6.2 | 80 | 82 | 4.8 |
| 4c- D | $[H_2F_3]^-$ | 5.9 | 80 | 83 | 5.1 |
| 4c- E | $[H_2F_3]^-$ | 5.8 | 100 | 105 | 5.1 |
| 4c- F | $[H_2F_3]^-$ | 5.8 | 100 | 102 | 5.3 |

As can be seen on comparison of the results of the comparative experiment series 1a to 1 d with those of the inventive experiment series 2-4, when the catalysts of the invention are used, a higher TOF is achievable quite generally than in the corresponding comparative experiments which were conducted at similar temperature and with an identical anion. It is additionally noticeable that, when the reaction temperature is increased in the inventive examples, the TOF rises and does not drop as it does in the comparative experiments. In the distillates, only an extremely small amount, if any, of catalyst breakdown products was to be found. This is not because of the fact that any breakdown products formed, because of their possibly relatively low volatility, do not go into the distillate in the distillative workup, as analytical studies on the resins having a low monomer content showed, which did not give any pointers at all to the presence of such breakdown products.

While polyisocyanate resins having very predominantly isocyanurate structures were obtained alongside a few uretdione, urethane, allophanate and iminooxadiazinedione groups when the catalysts having oxygen-containing anions were used, the catalysts containing fluorine in the anion gave products having iminooxadiazinedione structures alongside isocyanurate and the other aforementioned isocyanate conversion product structures. The proportion of iminooxadiazinedione groups rose significantly with higher fluorine content in the anion, i.e. at the transition from the simple fluorides to difluorides and trifluorides. At higher reaction temperature, it is reduced again, in favor of the formation of isocyanurate and (to an increased degree) uretdione. Uretonimines were not found in the resins of the invention even at high reaction temperature; in the products from the comparative experiments, they were detectable in traces at reaction temperatures above 80° C. and unambiguously above 100° C. (about 1-3 mol % based on the sum total of the isocyanate conversion products). At the same time, the residual monomer contents of the uretonimine-free resins were never above 0.1%, whereas those in the resins from the comparative experiments were much higher in some cases.

Examples 5a to 5d

Comparative Examples with CN 102964566

100 g of HDI in each case are heated to 60° C. and the following compounds are added in portions:

a) 2-(tert-butylimino)-N,N-diethyl-1,3-dimethyl-1,3,2lambda⁵-diazaphosphinan-2-amine b) N,N,N',N',N'',N''-hexamethyl-N'''-(2,4,4-trimethylpentan-2-yl)phosphorimidic triamide c) N'''-tert-butyl-N,N,N',N',N'',N''-hexamethylphosphorimidic triamide or d) 1-[N-tert-butyl-P,P-di(pyrrolidin-1-yl)phosphorimidoyl]pyrrolidine, in such a way that, after onset of the reaction, as indicated by slight exothermicity and/or a rise in the refractive index, stirring was continued initially without further addition of catalyst at 60° C. while monitoring $n_D$ and, if no further rise in the refractive index was recorded, the mixture was treated again with catalyst.

In all experiments, after a brief rise in the refractive index after addition of catalyst, no further reaction progress was apparent (stepped $n_D$-time profile), and so there is no point in reporting a turnover frequency.

By means of ³¹P NMR spectroscopy, it was found that the "catalyst" added, immediately after contact with the isocyanate, was converted quantitatively to the (carcinogenic) phosphoramides:

a) N,N-diethyl-1,3-dimethyl-1,3,2-diazaphosphinan-2-amine 2-oxide b) and c) N,N,N',N',N'',N''-hexamethylphosphoramide or d) 1,1',1''-phosphoryltripyrrolidine.

Analysis of the structural composition of the reaction mixtures with regard to the NCO conversion products in all cases showed proportions of uretonimine above 9 mol % (based on the sum total of the NCO conversion products) alongside isocyanurate (main component), iminooxadiazinedione and uretdione.

Distillative workup of the reaction mixtures was omitted because of the toxicological potential of the "catalyst" breakdown products.

Examples 6a to 6e

Comparative Examples with Acid Adducts onto Prior Art Neutral Bases

The procedure was as in comparative Example 5, using the following reagents:

a) tri-n-butylphosphine-HF adduct, 20% solution in 2-ethylhexanol b) pyridine-HF complex, 40% solution in iso-PrOH c) tri-n-butylamine-HF adduct, 25% solution in iso-PrOH d) tri-n-butylamine-acetic acid adduct, 40% solution in iso-PrOH e) tri-n-butylamine-water adduct, 40% solution in iso-PrOH or f) the adduct of the catalyst used in comparative example 5c (N'''-tert-butyl-N,N,N',N',N'',N''-hexamethylphosphorimidic triamide) and pivalic acid, 40% solution in THF.

In no case was any reaction of the isocyanate groups with one another observed—only (in the case of very high amounts of reagent added) conversion products of the stoichiometric reaction between isocyanate and reagent or the solvent thereof (HF adducts, acid amides, urethanes, etc.) were detectable.

Example 7

Inventive

The procedure was as in Example 1, except that the catalysts used were salts with tetrakis[cyclohexyl(methyl) amino]phosphonium cation, each as about 15% solutions in isopropanol/methanol, 1:1 (7a: fluoride, 2b: difluoride, 7c: trifluoride, 7d: acetate, 7e: pivalate). The results can be found in Table 6. In none of the distillates was the phosphorus content above the detection limit (about 1 ppm).

TABLE 6

| Example no. | | Catalyst anion | amount [g] | Reaction temperature [° C.] start | max. | TOF |
|---|---|---|---|---|---|---|
| 7a- | A | F⁻ | 4.5 | 60 | 69 | 0.7 |
| 7a- | B | F⁻ | 3.8 | 60 | 64 | 0.9 |
| 7a- | C | F⁻ | 3.8 | 80 | 85 | 1.1 |
| 7a- | D | F⁻ | 3.6 | 80 | 84 | 1.3 |
| 7a- | E | F⁻ | 3.5 | 100 | 102 | 1.5 |
| 7a- | F | F⁻ | 3.2 | 100 | 101 | 1.9 |
| 7b- | A | [HF₂]⁻ | 5.3 | 60 | 66 | 0.5 |
| 7b- | B | [HF₂]⁻ | 4.5 | 60 | 68 | 0.8 |
| 7b- | C | [HF₂]⁻ | 5.1 | 80 | 85 | 0.8 |
| 7b- | D | [HF₂]⁻ | 4.6 | 80 | 84 | 0.9 |
| 7b- | E | [HF₂]⁻ | 4.2 | 100 | 106 | 1.2 |
| 7b- | F | [HF₂]⁻ | 3.9 | 100 | 104 | 1.4 |
| 7c- | A | [H₂F₃]⁻ | 9.3 | 60 | 62 | 0.7 |
| 7c- | B | [H₂F₃]⁻ | 8.5 | 60 | 61 | 0.8 |
| 7c- | C | [H₂F₃]⁻ | 8.2 | 80 | 82 | 0.9 |
| 7c- | D | [H₂F₃]⁻ | 8.1 | 80 | 82 | 1.1 |
| 7c- | E | [H₂F₃]⁻ | 7.9 | 100 | 104 | 1.5 |
| 7c- | F | [H₂F₃]⁻ | 6.5 | 100 | 103 | 1.8 |
| 7d- | A | CH₃COO⁻ | 10.2 | 60 | 60 | 0.4 |
| 7d- | B | CH₃COO⁻ | 9.5 | 60 | 60 | 0.4 |
| 7d- | C | CH₃COO⁻ | 9.5 | 80 | 80 | 0.8 |
| 7d- | D | CH₃COO⁻ | 8.4 | 80 | 80 | 0.9 |
| 7d- | E | CH₃COO⁻ | 8.2 | 100 | 102 | 0.9 |
| 7d- | F | CH₃COO⁻ | 8.2 | 100 | 101 | 1.0 |
| 7e- | A | (CH₃)₃CCOO⁻ | 11.5 | 60 | 61 | 0.5 |
| 7e- | B | (CH₃)₃CCOO⁻ | 10.9 | 60 | 61 | 0.5 |
| 7e- | C | (CH₃)₃CCOO⁻ | 10.8 | 80 | 82 | 0.8 |
| 7e- | D | (CH₃)₃CCOO⁻ | 10.5 | 80 | 81 | 0.9 |
| 7e- | E | (CH₃)₃CCOO⁻ | 10.5 | 100 | 102 | 1.2 |
| 7e- | F | (CH₃)₃CCOO⁻ | 10.2 | 100 | 102 | 1.4 |

The foregoing examples of the present invention are offered for the purpose of illustration and not limitation. It will be apparent to those skilled in the art that the embodiments described herein may be modified or revised in various ways without departing from the spirit and scope of the invention. The scope of the invention is to be measured by the appended claims.

The invention claimed is:

1. A process for modifying isocyanates, comprising oligomerizing at least one monomeric organic isocyanate having an NCO functionality of >1 in the presence of at least one catalyst, wherein, the catalyst comprises compounds of the formula II (Formula II)

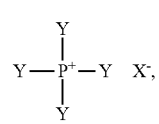

in which X⁻ is the anion of an acid having a pKa≥2, and wherein the cation of formula II corresponds to the following formula IV:

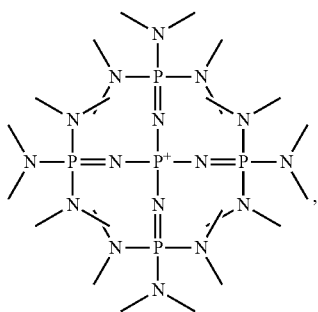
(Formula IV)

and X⁻ is selected from the group consisting of $F^-$, $HF_2^-$, $H_2F_3^-$ and mixtures thereof.

2. The process according to claim 1, wherein the acid corresponding to the anion X⁻ has a pKa≥2.5.

3. The process according to claim 1 wherein the oligomerization is conducted in the presence of a solvent or an additive.

4. The process according to claim 1, wherein the monomeric organic isocyanate comprises one or more aliphatic diisocyanates.

5. The process according to claim 1, wherein the process is conducted within the temperature range from 0° C. to +250° C.

6. The process according to claim 1, wherein the oligomerization is stopped after about 5% to about 80% by weight of the monomeric organic isocyanate used has been converted.

7. The process according to claim 6, wherein the oligomerization is stopped by deactivating the catalyst.

8. The process according to claim 6, wherein unconverted monomeric organic isocyanate is separated from the reaction mixture.

9. The process according to claim 2, wherein the acid corresponding to the anion X⁻ has a pKa≥3.0.

10. The process according to claim 2, wherein the acid corresponding to the anion X⁻ has a pKa≥3.10.

11. The process according to claim 4, wherein the one or more aliphatic isocyanates is/are selected from the group consisting of hexamethylene diisocyanate (HDI), 2-methylpentane 1,5-diisocyanate, 2,4,4-trimethylhexane 1,6-diisocyanate, 2,2,4-trimethylhexane 1,6-diisocyanate, 4-isocyanatomethyloctane 1,8-diisocyanate, 3(4)-isocyanatomethyl-1-methylcyclohexyl isocyanate (IMCI), isophorone diisocyanate (IPDI), 1,3- and 1,4-bis(isocyanatomethyl)benzene (XDI), 1,3- and 1,4-bis(isocyanatomethyl)cyclohexane (H6XDI) and mixtures thereof.

12. The process according to claim 5, wherein the process is conducted within the temperature range from about 20 to about 180° C.

13. The process according to claim 5, wherein the process is conducted within the temperature range from 40 to 150° C.

14. The process according to claim 6, wherein the oligomerization is stopped after about 10% to about 60% by weight of the monomeric organic isocyanate used has been converted.

15. The process according to claim 7, wherein the deactivation comprises adding an acid or an acid derivative, an acidic ester of phosphorus- or sulfur-containing acids to adsorptively bind the catalyst and removing the catalyst by filtration.

* * * * *